(12) United States Patent
Shrivastav et al.

(10) Patent No.: US 11,506,663 B2
(45) Date of Patent: Nov. 22, 2022

(54) METHIONINE AMINOPEPTIDASE OVEREXPRESSION IN THE PERIPHERAL BLOOD AND PERIPHERAL BLOOD MONONUCLEAR CELLS IS A MARKER FOR COLORECTAL CANCER SCREENING, DIAGNOSIS AND PROGNOSIS

(71) Applicant: VASTCON, Winnipeg (CA)

(72) Inventors: Shailly Shrivastav, Winnipeg (CA); Anuraag Shrivastav, Winnipeg (CA)

(73) Assignee: Vastcon, Winnipeg (CA)

( * ) Notice: Subject to any disclaimer, the term of this patent is extended or adjusted under 35 U.S.C. 154(b) by 519 days.

(21) Appl. No.: 15/309,891

(22) PCT Filed: May 13, 2015

(86) PCT No.: PCT/CA2015/050432
§ 371 (c)(1),
(2) Date: Nov. 9, 2016

(87) PCT Pub. No.: WO2015/172249
PCT Pub. Date: Nov. 19, 2015

(65) Prior Publication Data
US 2017/0242013 A1  Aug. 24, 2017

Related U.S. Application Data

(60) Provisional application No. 61/992,554, filed on May 13, 2014.

(51) Int. Cl.
*G01N 33/574* (2006.01)
*C12Q 1/37* (2006.01)
*G01N 33/573* (2006.01)
*G16H 50/30* (2018.01)

(52) U.S. Cl.
CPC ......... *G01N 33/57419* (2013.01); *C12Q 1/37* (2013.01); *G01N 33/573* (2013.01); *G01N 2333/948* (2013.01); *G16H 50/30* (2018.01)

(58) Field of Classification Search
None
See application file for complete search history.

(56) References Cited

U.S. PATENT DOCUMENTS

2010/0068731 A1* 3/2010 Sharma .................... C12Q 1/48
435/7.21
2013/0216494 A1* 8/2013 Petersen .............. C07D 303/18
424/78.27

FOREIGN PATENT DOCUMENTS

| EP | 1862803 | 12/2007 |
|---|---|---|
| WO | 2004057336 | 7/2004 |
| WO | 2007036025 | 4/2007 |
| WO | 2012033407 | 3/2012 |

OTHER PUBLICATIONS

Tucker et al., Ectopic expression of methionine aminopeptidase-2 causes cell transformation and stimulates proliferation, Oncogene (2008) 27, 3967-3976 (Year: 2008).*
Selvakumar'BBRC, Expression of methionine aminopeptidase 2, N-myristoyltransferase, and N-myristoyltransferase inhibitor protein 71 in HT29, Biochemical and Biophysical Research Communications 322 (2004) 1012-1017 (Year: 2004).*
Grdisa and Vitale, Types and Localization of Aminopeptidases in Different Human Blood Cells, Int. J. Biorhem. vol. 23. No. 3, pp. 339-345, 1991 (Year: 1991).*
Brenner et al., Potential for Colorectal Cancer Prevention of Sigmoidoscopy Versus Colonoscopy: Population-Based Case Control Study, Cancer Epidemiol Biomarkers Prev 2007; 16(3), Mar. 2007 (Year: 2007).*
Ho et al., MicroRNA profiling in pediatric pilocytic astrocytoma reveals biologically relevant targets, including PBX3, NFIB, and METAP2, Neuro-Oncology, vol. 15, Issue 1, Jan. 2013, pp. 69-82 (Year: 2013).*
Selvakumar P. et al: N-Myristoyltransferase 2 expression i human colon cancer: cross-talk btween the calpain and caspase system, FEBS Letters, vol. 580, No. 8, Apr. 2006, pp. 2021-2026.
Takamune N et al: Novel Strategy for anti-HIV-1 action: selective cytotoxic effect of N-Myristoyltransferase inhibitor on HIV-1-infected cells, FEBS Letters, vol. 527, No. 1-3, Sep. 11, 2002, pp. 138-142.
"Methionine Aminopeptidase 2 and Cancer"; Ponniah Selvakumar et al;Science Direct, Biochimica et Biophysica Acta 1760 (2006) 148-154.

* cited by examiner

*Primary Examiner* — Louise W Humphrey
*Assistant Examiner* — Srikanth Patury
(74) *Attorney, Agent, or Firm* — Michael R Williams; Kyle R Satterthwaite; Ade & Company Inc.

(57) ABSTRACT

A method of screening/prognosis/diagnosis for colorectal cancer (CRC) wherein methionine aminopeptidase 2 (MetAP2) levels are detected in a non-tumor sample such as peripheral blood, peripheral blood mononuclear cells (PBMC) or lymphocytes. Based on the MetAP2 levels, the individual may be selected for further testing.

1 Claim, 6 Drawing Sheets

METHIONINE AMINOPEPTIDASE OVEREXPRESSION IN THE PERIPHERAL BLOOD AND PERIPHERAL BLOOD MONONUCLEAR CELLS IS A MARKER FOR COLORECTAL CANCER SCREENING, DIAGNOSIS AND PROGNOSIS

PRIOR APPLICATION INFORMATION

The instant application is a 371 of PCT/CA2015/050432, filed May 13, 2015, which claimed the benefit of U.S. Provisional Patent Application, filed May 13, 2014, Ser. No. 61/992,554, entitled 'Methionine Aminopeptidase overexpression in the peripheral blood and peripheral blood mononuclear cells is a marker for colorectal cancer screening, diagnosis and prognosis", the contents of which are incorporated herein by reference.

BACKGROUND OF THE INVENTION

Colorectal cancer (CRC) is the third-leading cause of cancer deaths in Canada [1]. CRC arises slowly from pre-malignant adenomatous polyps. Since the cancer develops slowly there is a substantial window period during which either it or its precursor lesion (adenomatous polyps) can be detected. This permits treatment at the pre-malignant and early malignant stages. Over 90% of patients diagnosed with localized colorectal cancer survive more than five years. However, the majority of CRC cases are still diagnosed at an advanced stage [2, 3]. While CRC is the third most fatal cancer, there is a 90% chance of survival if treated at an early stage. Despite this, every year over 600,000 people around the world die of CRC [4]. These data indicate that there is an urgent unmet need for a reliable screening procedure for the early detection of CRC that can be easily implemented as a population based screening procedure for CRC.

Screening Strategies Available

Screening is the identification of the individuals who are at risk of developing CRC prior to the development of actual symptoms. The most common screening tests for CRC include Fecal Occult Blood Testing (FOBT), fecal immuno test (FIT), sigmoidoscopy and colonoscopy [5-7]. The compliance rate of these tests for screening is limited due to low sensitivity or the invasive nature of the test [8, 9]. For instance, although FOBT is cost effective and relatively safe, the rate of false positives are high because factors such as medication and diet might skew the results. For FOBT screening, patients must collect a stool sample at home and bring it to a laboratory for analysis. The reason for low compliance is the unpleasant nature of fecal sample collection. For example, during the first round of CRC screening in Manitoba, Canada, the uptake rate was a mere 15% of the targeted population between 50-75 years of age and in Ontario, Canada, the uptake was 29.3%, whereas 45.6% of the targeted population remained overdue for screening [10]. Sigmoidoscopy and colonoscopy are both expensive and invasive, and the results and risks of the procedure depend on the expertise of the attending endoscopist [11].

A widely available biomarker Carcinoembryonic Antigen (CEA) has limited sensitivity and specificity [12, 13]. A blood test is likely to be more readily acceptable than stool or endoscopic tests in a population-based screening procedure. Cost-effective blood tests may identify patients at high risk for CRC and improve patient compliance for more intensive and invasive diagnostic procedures.

Proteolysis and Metionine Aminopeptidase (MetAP)

Proteolysis is an important protein modification essential for normal functioning of cells and alterations in proteolysis have been implicated in various cancers. The most common processing events of nascent polypeptides are amino-terminal modifications occurring on almost every protein. Aminopeptidases belong to the metalloproteinase family and their function is to remove amino acids from unblocked N-termini of peptides or proteins.

Proteins synthesis is initiated by a start codon, which is methionine in eukaryotes and formylmethionine in prokaryotes. Methionine Aminopeptidases (MetAPs) catalyze the removal of methionine from the N-terminus of newly synthesized proteins [7]. Methionine removal is essential for further N-terminal modifications such as acetylation and myristoylation [14, 15]. In humans, MetAP exists in two isoforms: MetAP1 and MetAP2 coded by MetAP1 and MetAP2 genes, respectively. Both the isoforms differ from each other structurally, in substrate specificity and expression control, therefore, they are not redundant in function. MetAP1 is constitutively expressed, whereas MetAP2 is associated with cell proliferation. MetAP1 has a potential role in cell division, as inhibition of MetAP1 results in induction of apoptosis in HeLa as well as HT-1080 cell lines. A new subtype of MetAP1 namely, MetAP1D has been identified. MetAP1D has been demonstrated to be overexpressed in CRC patients and its inhibition results in decreased cell growth [16, 17]. MetAP2, apart from possessing aminopeptidase catalytic activity has an additional function as demonstrated earlier by Gupta, et. al [18]. Specifically, it regulates translation by protecting the α-subunit of eukaryotic initiation factor 2 (eIF2α) from phosphorylation [19]. Phosphorylation of eIF2α results in reduced translation initiation. MetAP2 expression correlates with cell growth and non-dividing cells do not show immunodetection levels of this protein. MetAP2 has been shown to be involved in the growth of different types of tumors [20]. MetAP2 cleaves methionine of the nascent c-Src, thus exposing its N-terminal glycine residue for myristoylation.

MetAP2 has been demonstrated to play a crucial role in angiogenesis. Angiogenesis is of particular importance as it is necessary for the progression of solid tumors and cancers. Several laboratories have demonstrated that the inhibition of MetAP results in regression of tumor growth and angiogenesis [21, 22]. MetAP2 has been identified as a molecular target of angiostatic agents such as fumagallin and ovalicin, which can bind to MetAP2 and inhibit its aminopeptidase activity [21, 23]. MetAP2 is implicated as having a role in cancer (Wang et al., 2008). Previous reports have shown MetAP2 overexpression in colon cancer, breast cancer, lung cancer, ovarian cancer, prostate cancer and hepatocarcinoma [24, 25]. There is some information available on the role of MetAP2 in cancer as reported by Tucker, et. al. who have proposed that MetAP2 ectopic expression causes cell transformation and promotes cell proliferation as MetAP2 inhibitors could reduce the cell transformation [26]. However, the expression of MetAP2 in immune response cells of a tumor bearing host is not known. Recently, we have identified that NMT2 isoform is overexpressed in the PBMCs of CRC patients. As MetAP2 is an upstream event of myristoylation, therefore, our interest was to study the status of MetAP2 in blood of CRC patients. There are no reports on the involvement of MetAP2 in the peripheral blood, PBMC and T cells of CRC patients. Herein it is reported for the first time the presence of MetAP2 in peripheral blood, PBMCs and I-cells. This study indicates that MetAP2 is overexpressed in the peripheral blood and PBMCs of CRC patients compared to healthy controls.

MetAP2 and CRC

Previous studies have investigated MetAP2 expression in tumors from CRC patients using IHC technique. MetAP2 also has been reported to show moderate staining in polyps. This staining is believed to reveal that MetAP2 is up regulated as part of the molecular events that take place during the malignant formation of colonic tissues [15]. Tucker et, al. also used IHC technique to study the expression of MetAP2 in adenocarcinomas of CRC samples [26]. These samples displayed moderate-to-strong staining for MetAP2. A study published by Kanno et al reported higher expression of MetAP2 in germinal centre B cells and their neoplastic counterparts [27]. The germinal centre is the site where B lymphocytes proliferate and undergo terminal differentiation through antigenic stimulation.

SUMMARY OF THE INVENTION

According to a first aspect of the invention, there is provided a method of screening for colorectal cancer (CRC) comprising:

detecting methionine aminopeptidase 2 (MetAP2) levels in a non-tumor sample from an individual at risk of developing CRC; and determining if MetAP2 levels are above a threshold value, wherein MetAP2 levels above the threshold value indicates that the individual is examined further for CRC.

MetAP2 levels above the threshold value may indicate that the individual has CRC.

The non-tumor sample may be peripheral blood or neutrophils or peripheral blood mononuclear cells (PBMC) or lymphocytes.

The threshold value may correspond to MetAP2 levels for a healthy individual.

DESCRIPTION OF THE PREFERRED EMBODIMENTS

Figure 1:
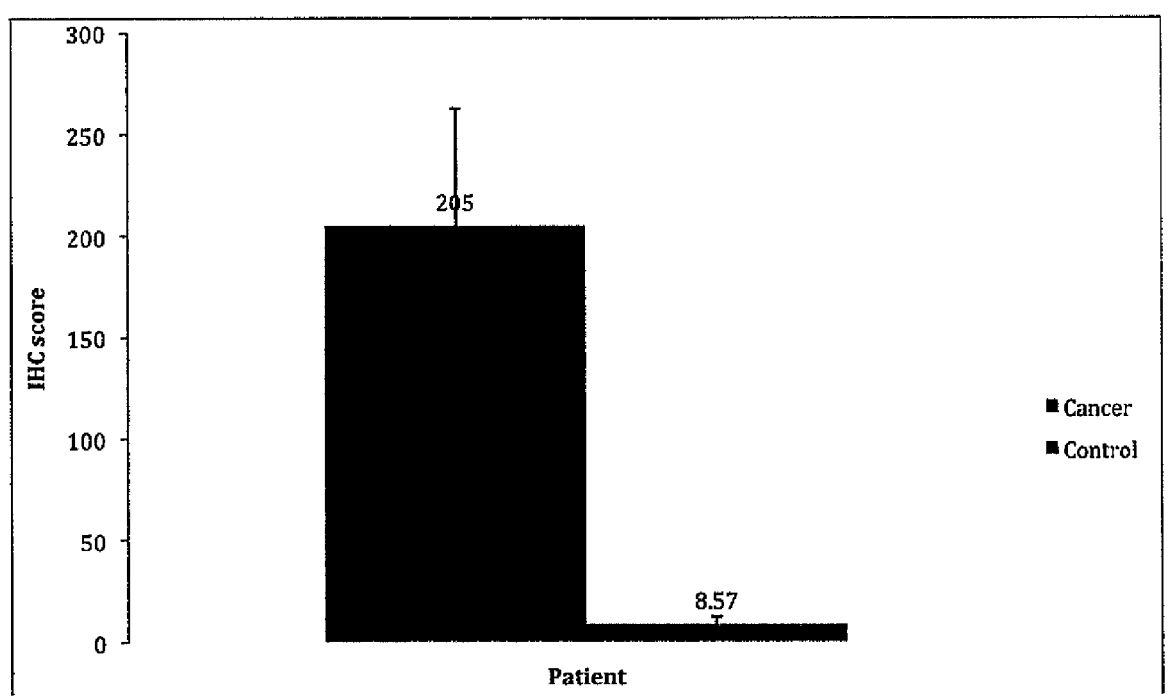
FIG. 1: Average IHC score of eight cancer and seven control subjects stained for MetAP2. The average IHC score for CRC samples was 205±57.56 and the average IHC score for control samples was 8.57±3.78. The bars on the graph present the standard deviations of the data.
Figure 2:
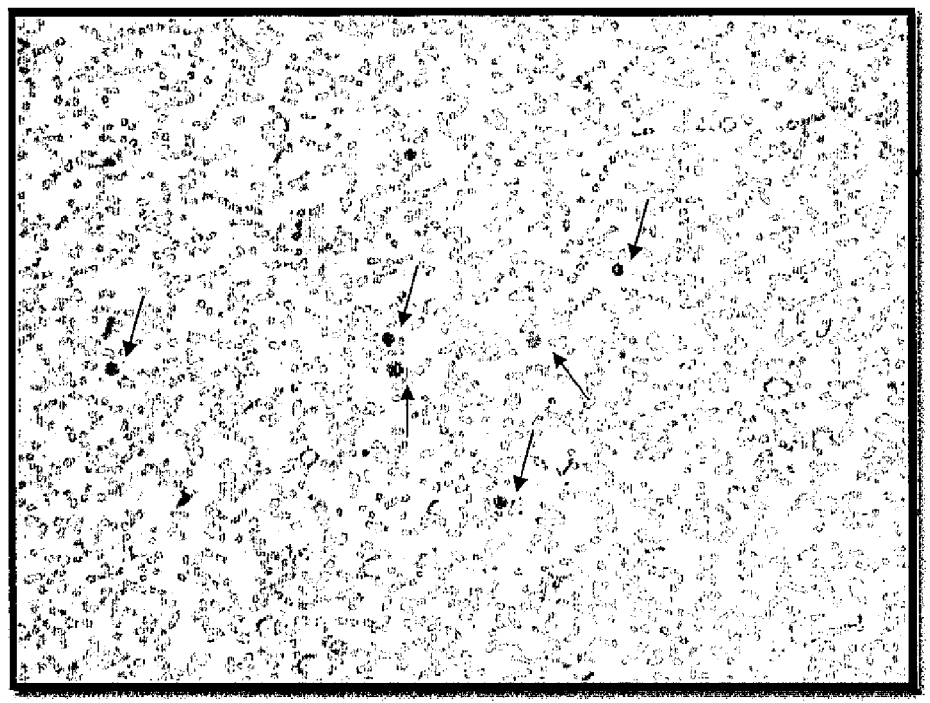
FIG. 2: Immunohistochemical analysis of peripheral blood for CRC patient ID0023. PB cells were incubated with anti-MetAP2 antibody (brown positive staining). Black arrows are pointing to positively stained lymphocyte, grey arrows are pointing to positively stained neutrophil. (20×)
Figure 3:
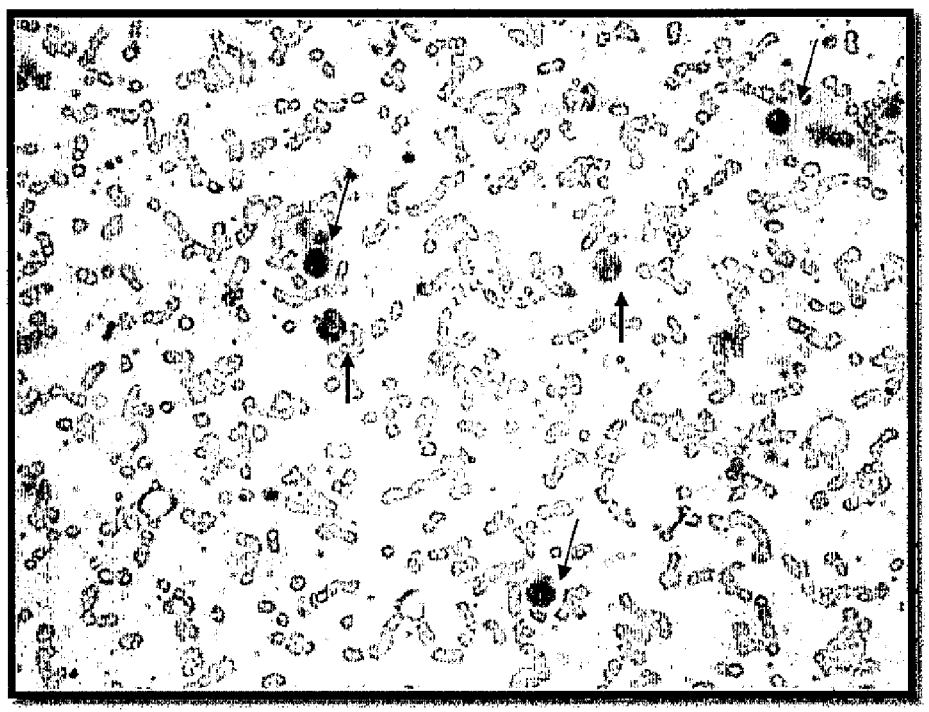
FIG. 3: Immunohistochemical analysis of peripheral blood for CRC patient ID0023. PB cells were incubated with anti-MetAP2 antibody. Black arrows are pointing to positively stained lymphocyte, grey arrows are pointing to positively stained neutrophil. (40×)
Figure 4:
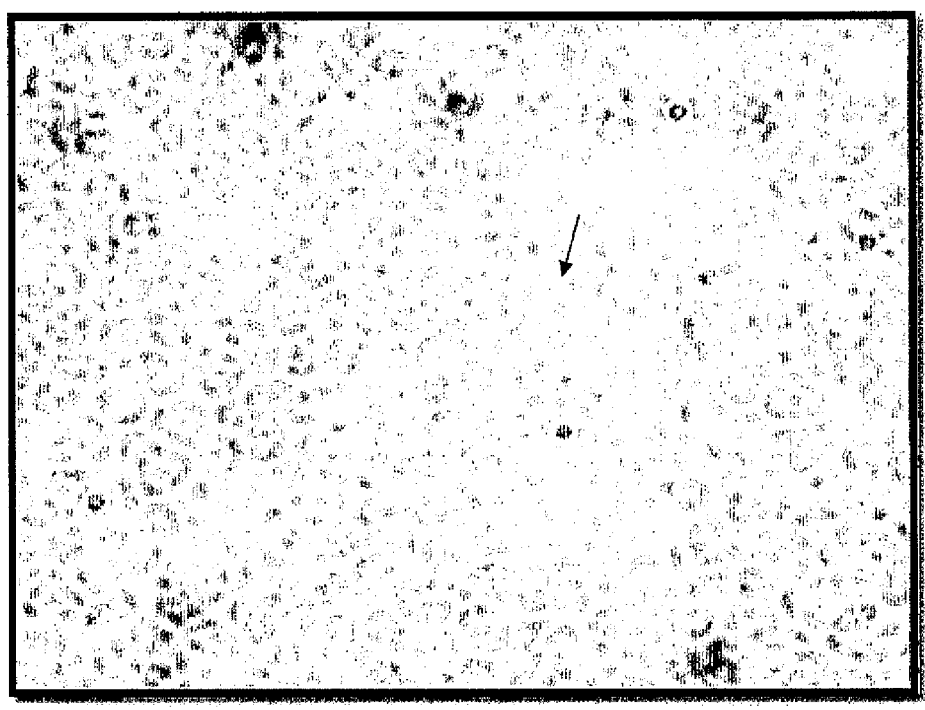
FIG. 4: Immunohistochemical analysis of peripheral blood for control healthy subject ID0006. PB cells were incubated with anti-MetAP2 antibody. Black arrow is pointing to negatively stained lymphocyte. (40×)
Figure 5:
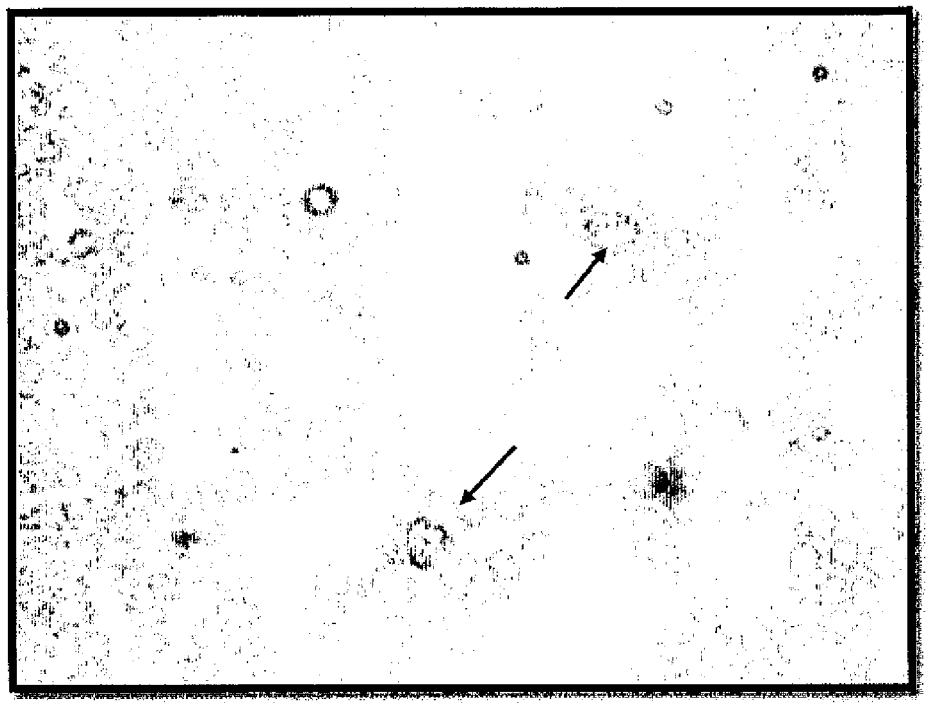
FIG. 5: Immunohistochemical analysis of peripheral blood for control patient ID0006. PB cells were incubated with anti-MetAP2 antibody. This is a different field of vision of control subject ID0006 depicted in FIG. 4. Grey arrows are pointing to weakly positive stained neutrophil. (40×)
Figure 6:
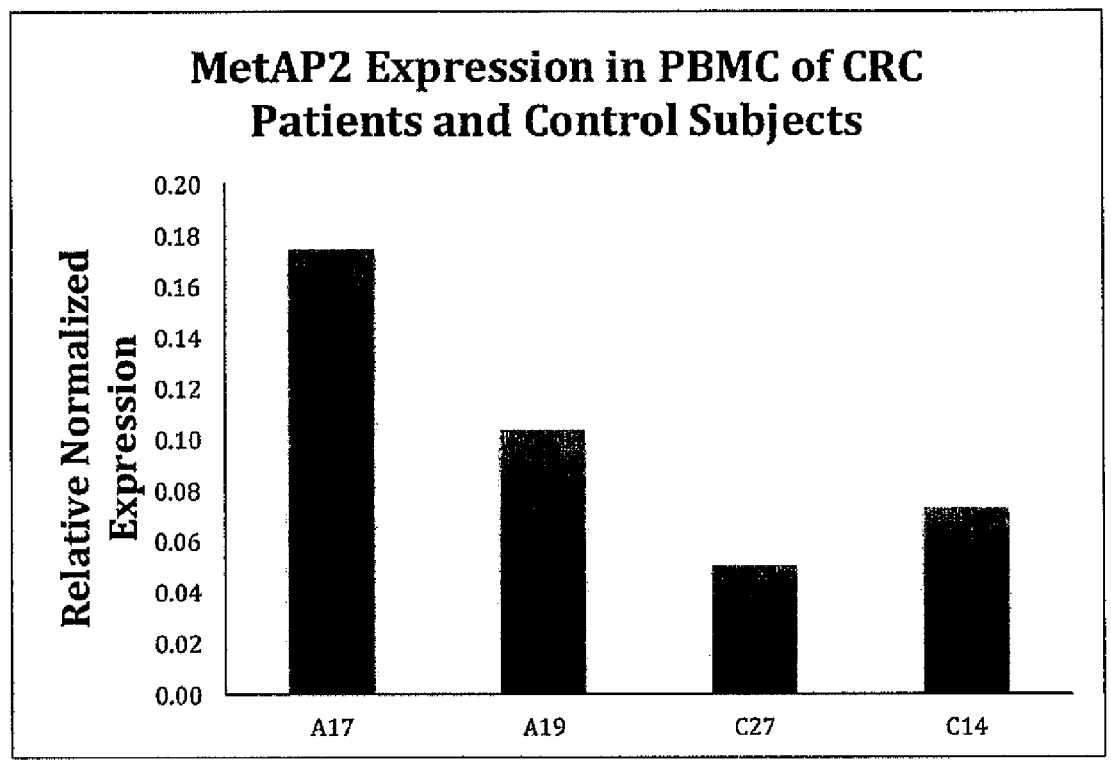
FIG. 6. Methionine Aminopeptidase 2 (MetAP2) gene expression profile in CRC patients and healthy subjects. MetAP2 gene expression in the peripheral blood mononuclear cells was determined in CRC patients (A17 and A19) and healthy subjects (C27 and C14) by quantitative real time polymerase chain reaction (qRT-PCR) using validated PCR Prime primers from BioRad. These primers were specific for MetAP2. The expression of MetAP2 gene in CRC patients is approximately twice as compared to healthy subjects.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Our earlier studies indicated that NMT is overexpressed and is hyperactive in peripheral blood mononuclear cells (PBMC) of CRC patients. NMT exists as NMT1 and NMT2. Recently, we have demonstrated that it is the NMT2 isoform that is overexpressed in the PBMCs of CRC patients in comparison with healthy control subjects. Our interest was to see if this altered NMT2 overexpression in PBMCs of CRC patients is also associated with alterations in expression of MetAP2 as it is an upstream target of NMT2. Our aim was to study the expression of MetAP2 in peripheral blood and PBMCs of CRC patients and whether it can serve as a marker for screening, diagnosis or prognosis for CRC.

To study the level of MetAP2 in PBMC of CRC patients, a validated monoclonal anti-MetAP2 antibody (available from Santa Cruz Biotechnology, Inc, USA) was used to determine the MetAP2 expression profile. Immunohistochemistry (IHC) technique was used to determine the expression of MetAP2 in the peripheral blood smears of CRC patients. IHC analysis not only provides information on the expression of MetAP2 but also the localization of MetAP2 in various cells in the blood smear. IHC score or H score were given to the expression level of MetAP2 expression in the peripheral blood smears from CRC patients and were compared with blood smears from healthy control subjects. IHC score was calculated as the multiplication of intensity (on a scale of 0-3) and percentage positive cells (0-100%) therefore giving a minimum of IHC=0 and maximum of IHC=300. Our study reveals the overexpression of MetAP2 in non-tumor tissue such as peripheral blood, PBMCs, neutrophils and lymphocytes of CRC patients in comparison with healthy subjects. Therefore it can serve as a biomarker for screening/diagnosis/prognosis of CRC, as discussed herein.

Earlier studies have been performed using IHC technique to evaluate the expression of MetAP2 in CRC tumors tissues. MetAP2 shows moderate staining in polyps from CRC patients, indicative of the fact that MetAP2 is up regulated as part of the molecular events that take place during the malignant formation of colonic tissues [15]. Tucker et al [26] also used IHC technique to determine expression of MetAP2 in adenocarcinomas of colorectal tumor samples and their study displayed a moderate-to-strong staining for MetAP2.

The present study is the first investigation showing MetAP2 overexpression in the peripheral blood, neutrophils, PBMC and lymphocytes of CRC patients.

We also investigated the type of cells within the peripheral blood cells that showed a pattern of intense staining. Our results indicate that MetAP2 showed a positive staining in lymphocytes and neutrophils of peripheral blood from CRC patients. In our study we quantified the expression of MetAP2 by providing IHC scores, as discussed herein.

As will be appreciated by one of skill in the art, overexpression of MetAP2 in peripheral blood and PBMC of CRC patients is surprising. Overexpression of MetAP2 in non-tumor tissue such as peripheral blood or immune response cells such as PBMC, neutrophil and lymphocyte establishes its potential role in onset and progression of CRC. While not wishing to be bound to a particular theory or hypothesis, it is noted that given the fact that PBMC usually consist of ~70% T-cells, it is possible that MetAP2 overexpression in a high proportion of PBMC of CRC patients implies overexpression of this enzyme in large numbers of T-cells of potentially diverse antigenic specificities rather than only in those specific to CRC. MetAP2 overexpression exclusively in CRC-driven clonally expanded CRC-specific T-cells may not be a favoured scenario, although this possibility cannot at present be ruled out.

According to an aspect of the invention, there is provided a method of screening for colorectal cancer (CRC) comprising:
  detecting methionine aminopeptidase 2 (MetAP2) levels in a non-tumor sample from an individual at risk of developing CRC or at risk of having CRC; and
  determining if MetAP2 levels are above a threshold value,
  wherein MetAP2 levels above the threshold value indicates that the individual is examined for CRC.

For example, the individual may be screened further for CRC or may have additional tests to confirm that the individual has CRC.

According to another aspect of the invention, there is provided a method of screening for colorectal cancer (CRC) comprising:
  detecting methionine aminopeptidase 2 (MetAP2) levels in a non-tumor sample from an individual at risk of developing CRC or at risk of having CRC; and
  determining if MetAP2 levels are above a threshold value,
  wherein MetAP2 levels above the threshold value indicates that the individual has CRC.

In some embodiments, the non-tumor sample is peripheral blood, neutrophils, peripheral blood mononuclear cells (PBMC) and/or lymphocytes.

In some embodiments, the threshold value corresponds to MetAP2 levels for a healthy individual. As will be appreciated by one of skill in the art, this control level would not need to be determined or repeated every time.

An individual at risk of developing colorectal cancer may be any individual who is over 50 years of age and/or may be an individual who has a familial history of colorectal cancer or who is considered to have a high likelihood of developing the disease.

As will be appreciated by one of skill in the art, this method may be used to screen for individuals who have MetAP2 levels above a threshold level and who consequently should be examined with other rigorous procedures for colorectal cancer. However, the method can also be used to diagnose or identify individuals with colorectal cancer based on the MetAP2 levels in their peripheral blood sample or peripheral blood mononuclear cells.

Similarly, the method can be used for prognosis of colorectal cancer in that particularly high MetAP2 levels may indicate a particularly aggressive stage of cancer.

As will be appreciated by one of skill in the art, the ability to screen peripheral blood samples for colorectal cancer represents a significant improvement over the prior art, which, as discussed above, suffers from low compliance. Specifically, the ability to screen peripheral blood samples means that individuals could be screened for colorectal cancer during routine or annual blood work for cholesterol, diabetes and other diseases.

Identification of biomarkers in the blood for the screening individuals with or at risk of developing CRC is attractive as it would not only increase compliance but also would reduce plausible deterioration of lifestyle after diagnosis. As discussed above, MetAP2 has been studied and has been identified in solid tumour tissues; however, there are no prior reports on the presence of MetAP2 in the human blood. A report on the essential role of MetAP2 in hematopoiesis has been demonstrated in zebrafish model [28]; however, there are no prior studies reporting MetAP in human blood cells or any of the blood cell precursor(s) or their lineages. This is the first report demonstrating the presence of MetAP2 in human peripheral blood, PBMCs, neutrophils and lymphocytes (specifically T-lymphocytes).

MetAP2 has also been shown to be required for hematopoietic stem cell initiation and proliferation [28]. The authors demonstrated that MetAP2 activity could significantly reduce definitive hematopoiesis and perturbed angiogenesis in zebrafish development using fumagillin treatment and morpholino gene knockout. The study also found that these treatments reduced MetAP2 levels in the hematopoietic stem and progenitor cells (HSPCs) activity in enriched $CD34^+$ cells suggesting an essential role of MetAP2 in hematopoiesis. From these observations it can be concluded that MetAP2 may play a cell autonomous role in maintaining HSPC activity. Overexpression of MetAP2 in blood cells may indicate that MetAP2 activity/expression in hematopeitic cells are altered in CRC and is reflective in peripheral blood and/or PBMC. However, the possibility that alteration in $MetAP_2$ activity/expression in the HSPCs are responsible for the development and/or progression of CRC cannot be ruled out.

Previous studies have investigated the relationship between NMT and MetAP2 in human colon cancer cell lines. A high level of NMT and MetAP in Colo320, Colo201 and Colo205 were observed by Selvakumar et al, [24]. The enzyme expression and activity varied with cell density (confluency of cells or number of cells in culture dish). For NMT and MetAP, higher enzyme activity and expression was observed at low cell density (10%), whereas Src expression level was greatly reduced in low density cells. The results were interpreted as an indication that NMT and MetAP upregulation as a part of the early stages of molecular events that take place during the overproduction of oncoproteins.

There are no reports on the expression of MetAP2 in blood. Our study shows that MetAP2 expression in blood can serve as a novel potential molecular marker for the screening of CRC in the form of a blood test. Blood test for CRC detection would also increase the compliance rates in comparison to the existing non-specific tests.

PBMCs from peripheral blood samples of eight cancer patients and seven healthy individuals were stained for MetAP2. The results are tabulated in Table 1 and Table 2, respectively. The different types of cells within PBMC's such as lymphocytes and monocytes were not differentially scored, these scores only represent an average of all PBMC as well as neutrophils.

An independent-sample t-test on IHC scores from the blood of CRC patient samples and control patient was performed. A significant difference in the IHC scores for CRC patient (Mean=205, Standard deviation=57.56983) and healthy controls (Mean=8.57, Standard Deviation=3.78); $t=6.27 \times 10^{-7}$, $p<0.001$ was observed. The IHC score of MetAP2 in the blood samples from CRC patients showed ~24-folds higher expression than that of healthy control.

While the preferred embodiments of the invention have been described above, it will be recognized and understood that various modifications may be made therein, and the appended claims are intended to cover all such modifications which may fall within the spirit and scope of the invention.

TABLE 1

Colorectal cancer patients peripheral blood stained for MetAP2. Values represent the score for percentage of positively stained cells (0-100%), the intensity of the positive stain (0-3) and the IHC score (% positive cells × intensity).

| Patient ID | Cell type | Antibody | Intensity | Percentage | IHC score |
|---|---|---|---|---|---|
| ID0017 | PB | MetAP2 | 3 | 90 | 270 |
| ID0019 | PB | MetAP2 | 3 | 70 | 210 |
| ID0020 | PB | MetAP2 | 2 | 75 | 150 |
| ID0021 | PB | MetAP2 | 3 | 90 | 270 |
| ID0023 | PB | MetAP2 | 3 | 90 | 270 |
| ID0024 | PB | MetAP2 | 2 | 80 | 160 |
| CRC-BCB00266116 | PB | MetAP2 | 2 | 70 | 140 |
| ID0014 | PB | MetAP2 | 2 | 85 | 170 |

TABLE 2

Healthy control peripheral blood stained for MetAP2. Values represent the score for percentage of positively stained cells (0-100%), the intensity of the positive stain (0-3) and the IHC score (% positive cells × intensity).

| Patient ID | Cell type | Antibody | Intensity | Percentage | IHC score |
|---|---|---|---|---|---|
| ID0006 | PB | MetAP2 | 1 | 5 | 5 |
| ID0008 | PB | MetAP2 | 1 | 10 | 10 |
| ID0009 | PB | MetAP2 | 1 | 15 | 15 |
| ID0010 | PB | MetAP2 | 1 | 10 | 10 |
| ID0012 | PB | MetAP2 | 1 | 5 | 5 |
| UWAS1 | PB | MetAP2 | 1 | 10 | 10 |
| UWAS2 | PB | MetAP2 | 1 | 5 | 5 |

REFERENCES

1. Canadian Cancer Society's Steering Committee on Statistics. Canadian Cancer Statistics 2012. 2012.
2. Manitoba CC: Cancer in Manitoba: Incidence and Mortality *Annual Stastical Report* 2004:1-67.
3. Anonymous: Population screening for colorectal cancer. *Drug and Therapeutics Bulletin* 2006, 44:65-68.
4. Canadian Cancer Society's Steering Committee. 2010. Canadian Cancer Statistics 2010. 2010:1-127.
5. Colorectal cancer screening. Recommendation statement from the Canadian Task Force on Preventive Health Care. *CMAJ* 2001, 165(2):206-208.
6. Colorectal cancer screening. Recommendation statement from the Canadian task force on preventive health care. *Can Fam Physician* 2001, 47:1811-1813, 1815.
7. Winawer S, Fletcher R, Rex D, Bond J, Burt R, Ferrucci J, Ganiats T, Levin T, Woolf S, Johnson D et al: Colorectal cancer screening and surveillance: clinical guidelines and rationale-Update based on new evidence. *Gastroenterology* 2003, 124(2):544-560.
8. Moayyedi P: Colorectal cancer screening lacks evidence of benefit. *Cleve Clin J Med* 2007, 74(8):545, 549-550, 552 passim.
9. Nicholson F B, Barro J L, Atkin W, Lilford R, Patnick J, Williams C B, Pignone M, Steele R, Kamm M A: Review article: Population screening for colorectal cancer. *Ailment Pharmacol Ther* 2005, 22(11-12): 1069-1077.
10. Rabeneck L, Tinmouth J M, Paszat L F, Baxter N N, Marrett L D, Ruco A, Lewis N, Gao J: Ontario's Colon-CancerCheck: Results from Canada's First Province-Wide Colorectal Cancer Screening Program. *Cancer Epidemiol Biomarkers Prev* 2014, 23(3):508-515.
11. Baxter N N, Goldwasser M A, Paszat L F, Saskin R, Urbach D R, Rabeneck L: Association of colonoscopy and death from colorectal cancer. *Ann Intern Med* 2009, 150(1):1-8.
12. Duffy M J, van Dalen A, Haglund C, Hansson L, Klapdor R, Lamerz R, Nilsson O, Sturgeon C, Topolcan O: Clinical utility of biochemical markers in colorectal cancer: European Group on Tumour Markers (EGTM) guidelines. *Eur J Cancer* 2003, 39(6):718-727.
13. Ouyang D L, Chen J J, Getzenberg R H, Schoen R E: Noninvasive testing for colorectal cancer: a review. *Am J Gastroenterol* 2005, 100(6):1393-1403.
14. Selvakumar P, Lakshmikuttyamma A, Shrivastav A, Das S B, Dimmock J R, Sharma R K: Potential role of N-myristoyltransferase in cancer. *Prog Lipid Res* 2007, 46(1):1-36.
15. Selvakumar P, Lakshmikuttyamma A, Dimmock J R, Sharma R K: Methionine aminopeptidase 2 and cancer. *Biochim Biophys Acta* 2006, 1765(2):148-154.
16. Mauriz J L, Martin-Renedo J, Garcia-Palomo A, Tunon M J, Gonzalez-Gallego J: Methionine aminopeptidases as potential targets for treatment of gastrointestinal cancers and other tumours. *Curr Drug Targets* 2010, 11(11):1439-1457.
17. Leszczyniecka M, Bhatia U, Cueto M, Nirmala N R, Towbin H, Vattay A, Wang B, Zabludoff S, Phillips P E: MAP1D, a novel methionine aminopeptidase family member is overexpressed in colon cancer. *Oncogene* 2006, 25(24):3471-3478.
18. Datta B, Chakrabarti D, Roy A L, Gupta N K: Roles of a 67-kDa polypeptide in reversal of protein synthesis inhibition in heme-deficient reticulocyte lysate. *Proc Natl Acad Sci USA* 1988, 85(10):3324-3328.
19. Ray M K, Datta B, Chakraborty A, Chattopadhyay A, Meza-Keuthen S, Gupta N K: The eukaryotic initiation factor 2-associated 67-kDa polypeptide (p67) plays a critical role in regulation of protein synthesis initiation in animal cells. *Proc Natl Acad Sci USA* 1992, 89(2):539-543.
20. Boxem M, Tsai C W, Zhang Y, Saito R M, Liu J O: The *C. elegans* methionine aminopeptidase 2 analog map-2 is required for germ cell proliferation. *FEBS Lett* 2004, 576(1-2):245-250.
21. Griffith E C, Su Z, Turk B E, Chen S, Chang Y H, Wu Z, Biemann K, Liu J O: Methionine aminopeptidase (type 2) is the common target for angiogenesis inhibitors AGM-1470 and ovalicin. *Chem Biol* 1997, 4(6):461-471.
22. Chun E, Han C K, Yoon J H, Sim T B, Kim Y K, Lee K Y: Novel inhibitors targeted to methionine aminopeptidase 2 (MetAP2) strongly inhibit the growth of cancers in xenografted nude model. *Int J Cancer* 2005, 114(1): 124-130.
23. Sin N, Meng L, Wang M Q, Wen J J, Bornmann W G, Crews C M: The anti-angiogenic agent fumagillin covalently binds and inhibits the methionine aminopeptidase, MetAP-2. *Proc Natl Acad Sci USA* 1997, 94(12):6099-6103.

24. Selvakumar P, Lakshmikuttyamma A, Lawman Z, Bonham K, Dimmock J R, Sharma R K: Expression of methionine aminopeptidase 2, N-myristoyltransferase, and N-myristoyltransferase inhibitor protein 71 in HT29. *Biochem Biophys Res Commun* 2004, 322(3):1012-1017.
25. Sheen I S, Jeng K S, Jeng W J, Jeng C J, Wang Y C, Gu S L, Tseng S Y, Chu C M, Lin C H, Chang K M: Fumagillin treatment of hepatocellular carcinoma in rats: an in vivo study of antiangiogenesis. *World J Gastroenterol* 2005, 11(6):771-777.
26. Tucker L A, Zhang Q, Sheppard G S, Lou P, Jiang F, McKeegan E, Lesniewski R, Davidsen S K, Bell R L, Wang J: Ectopic expression of methionine aminopeptidase-2 causes cell transformation and stimulates proliferation. *Oncogene* 2008, 27(28):3967-3976.
27. Kanno T, Endo, H., Takeuchi, K., Morishita, Y., Fukayama, M., Mori, S.: High expression of methionine aminopeptidase type 2 in germinal center B cells and their neoplastic counterparts. *Laboratory Investigation* 2002, 82:893-901.
28. Ma A C, Fung T K, Lin R H, Chung M I, Yang D, Ekker S C, Leung A Y: Methionine aminopeptidase 2 is required for HSC initiation and proliferation. *Blood* 2011, 118(20): 5448-5457.

The invention claimed is:

1. A method of screening for colorectal cancer (CRC) comprising:

detecting methionine aminopeptidase 2 (MetAP2) levels in a non-tumor sample from an individual at risk of developing CRC, said non-tumor sample selected from the group consisting of peripheral blood, peripheral blood mononuclear cells, neutrophils, and lymphocytes;

identifying individuals based on the MetAP2 levels in their non-tumor samples above a threshold value corresponding to MetAP2 levels for a healthy individual; and examining the individual with MetAP2 levels above the threshold value by colonoscopy or sigmoidoscopy for CRC.

* * * * *